United States Patent [19]

Oshiyama

[11] Patent Number: 5,149,327

[45] Date of Patent: Sep. 22, 1992

[54] MEDICAL VALVE, CATHETER WITH VALVE, AND CATHETER ASSEMBLY

[75] Inventor: Hiroaki Oshiyama, Kanagawa, Japan

[73] Assignee: Terumo Kabushiki Kaisha, Tokyo, Japan

[21] Appl. No.: 568,198

[22] Filed: Aug. 15, 1990

[30] Foreign Application Priority Data

Sep. 5, 1989 [JP] Japan ............................. 1-103482[U]
Sep. 29, 1989 [JP] Japan ................................ 1-252289

[51] Int. Cl.$^5$ ............................................. A61M 25/00
[52] U.S. Cl. ................................... 604/167; 604/256; 251/149.1
[58] Field of Search ............. 604/164, 167, 169, 247, 604/256; 251/149.1; 137/843, 844, 849

[56] References Cited

U.S. PATENT DOCUMENTS

| | | | |
|---|---|---|---|
| 3,585,996 | 6/1971 | Reynolds et al. | 604/158 |
| 4,143,353 | 3/1979 | Abramson | 251/149.1 |
| 4,314,555 | 2/1982 | Sagae | 604/167 |
| 4,610,665 | 9/1986 | Matsumoto et al. | 604/256 |
| 4,626,245 | 12/1986 | Weinstein | 604/256 |
| 4,798,594 | 1/1989 | Hillstead | 604/167 |
| 4,817,631 | 4/1989 | Schnepp-Pesch et al. | 604/167 |
| 4,844,087 | 7/1989 | Garg | 604/169 |
| 4,895,565 | 1/1990 | Hillstead | 604/256 |
| 4,932,633 | 6/1990 | Johnson et al. | 604/256 |
| 5,009,391 | 4/1991 | Steigerwald | 604/247 |
| 5,041,095 | 8/1991 | Littrell | 251/149.1 |

FOREIGN PATENT DOCUMENTS 0171077 2/1986 European Pat. Off. .

Primary Examiner—Gene Mancene
Assistant Examiner—Michael Lynch

[57] ABSTRACT

A medical valve comprises a valve member made of a flexible elastic material and having at least two faces. A first slit is disposed between a first face of said at least two faces and a second face of said at least two faces, and a second slit is disposed between said first face and said second face, wherein the first slit and the second slit intersect each other. A first opening width of the first slit on the first face is different from a second opening width of the first slit on the second face, and a first opening width of the second slit on the first face is different from a second opening width of the second slit on the second face. A catheter assembly comprises a catheter and a connecting instrument. The catheter includes a hollow body introducible into a blood vessel and a proximal member communicating with a hollow portion of the hollow body, the proximal member having an introduction passage in which a valve is disposed therein. The connecting instrument includes a tubular portion connectable to the introduction passage and insertable in a liquid sealing manner through the valve disposed in the introduction passage. The distal end of the tubular portion of the connecting instrument is disposed adjacent to an inner surface of the interior of the hollow body of the catheter when the connecting instrument is connected to the introduction passage of the proximal member of the catheter.

16 Claims, 6 Drawing Sheets

MEDICAL VALVE, CATHETER WITH VALVE, AND CATHETER ASSEMBLY

BACKGROUND OF THE INVENTION

1. Field of the Invention

The present invention relates to a medical valve, a catheter with a valve, and a catheter assembly.

2. Prior Art (A) In general, into a medical instrument, such as a catheter or the like, a tubular member, for example, a guide wire for introducing and guiding the catheter into organs in the human body, an injector for injecting medicine or the like into a specific organ, and an extractor for extracting body fluid from an organ through the catheter, can be inserted. In particular, in the case of circulatory support for acute heart failure, since it is rapid, it is necessary to percutaneously assure a blood vessel thereby. Furthermore, in such a medical instrument, the tubular member can be inserted in a liquid sealing manner into a passage capable of passing the tubular member therethrough, and a valve, which is closed when the tubular member is not inserted in the passage, is mounted so as to prevent liquid leakage from the passage.

For example, medical valves of the following two types "a" and "b" are known: The type "a" has, as disclosed in U.S. Pat. No. 4,798,594, a plurality of slits which penetrate from one end face to the other end face and intersect one another, and the type "b" has, as disclosed in Japanese Unexamined Patent No. 59-133877, a first slit which opens at only one end face and a second slit which opens at only the other end face, the two slits intersecting each other inside the valve.

(B) Patients suffering from heart failure, e.g. myocardial infarction, have hitherto been treated by various methods such as percutaneous transluminal coronary angioplasty (hereinafter abbreviated to "PTCA"), and Intra Aortic Balloon Pumping (hereinafter abbreviated to "IABP").

In PTCA, a balloon is inserted into the constricted lesion of the coronary artery, and is then inflated to dilate the constricted lesion.

In IABP, a balloon is inserted in the base portion of the aorta, and is then repeatedly inflated and deflated in synchronization with the heart beat to increase blood flow in the coronary artery, hence, to assist a heart whose function has degraded.

Problems to be Overcome by the Invention (A) However, in the case of the conventional valve of the above type "a", the restitutive force of each slit from the open state to the closed state is small. Therefore, while the tubular member is indwelling in the valve, the adhesive force of each slit to the periphery of the tubular member is small and it is likely that liquid leakage will result. Furthermore, when the tubular member is withdrawn, since the restitutive force of each slit to the closed state is small, each slit does not become closed immediately after the tubular member is withdrawn and it is likely that the liquid will leak.

On the other hand, in the conventional valve of the above type "b", the restitutive force of each slit from the open state to the closed state and the liquid sealing characteristic are high when the tubular member is indwelling and then withdrawn. However, since no slit penetrates between the two end faces of the valve, it allows only a tubular member, whose inserted distal end portion is fine, to be inserted therein.

An object of the present invention is to provide a medical valve into which even a tubular member whose inserted distal end portion is thick can be inserted and whose liquid sealing characteristic is high both when the tubular member is indwelling and when the tubular member is withdrawn.

Another object of the present invention is to provide a method which can easily produce the above valve.

Still another object of the present invention is to provide a catheter which has the above valve and which can with certainty prevent fluid from leaking from an opening at its proximal part.

(B) The conventional methods involve the following problems: ① PTCA treatment may put a patient into a shocked condition, which is very dangerous; and ② IABP treatment can increase blood flow only to a limited extent because the heart assisting function can be degraded with a drop in the cardiac output, sometimes failing to assure the patient's recovery.

Because of the problems ① and ②, it is sometimes necessary for heart treatment to be performed simultaneously with cardiopulmonory bypass of the blood, wherein an extracorporeal blood circulation circuit is formed for this purpose during the heart treatment.

During the treatment of heart failure, e.g. acute myocardial infarction, because the heart function is degraded, emergency cardiopulmonory bypass is performed to add oxygen and remove carbon dioxide.

In such cases where cardiopulmonory bypass is necessary, there is too little time to form the circuit by open heart surgery.

In such cases, therefore, catheters capable of percutaneous insertion are employed to allow blood to be drawn from and pumped back into the patient's body through the catheters, thereby effecting extracorporeal circulation.

However, with a conventional catheter device, since percutaneous insertion is conducted, the diameter of a catheter is inevitably small, thereby involving a great resistance to the flow of blood, hence, a great pressure loss. Thus, it is difficult to assure sufficient amounts of drawn-out blood and pumped-in blood.

An object of the present invention is to provide a catheter assembly that has a diameter small enough to facilitates percutaneous insertion at the time of circulatory support but that is capable of assuring sufficient amounts of drawn-out and pumped-in blood.

DISCLOSURE OF THE INVENTION

The present invention relates to a medical valve made of a flexible elastic material having at least two faces, and which comprises

- a first slit disposed from one face of the two faces to the other face of the two faces; and
- a second slit disposed from the one face to the other face,
- wherein the first slit and the second slit cross each other,
- wherein first and second opening widths which the first slit has on the two faces respectively are different from each other,
- wherein first and second opening widths which the second slit has on the two faces respectively are different from each other.

The present invention further relates to a medical valve, wherein the face which has the shorter opening width of the two opening widths of the first slit and the face which has the shorter opening width of the two opening widths of the second slit are different from each other.

The present invention still further relates to a medical valve, wherein the face which has the shorter opening width of the two opening widths of the first slit and the face which has the shorter opening width of the two opening widths of the second slit are same each other.

The present invention still further relates to a method of producing a medical valve, wherein the first and second slits are formed by winding a valve material around a cylindrical member so that one face of the valve material is in tight contact with the outer periphery of the cylindrical member, making a cut substantially perpendicular to the direction of the shaft of the cylindrical member by a cutting means from the other face to the face in tight contact with the cylindrical member of the valve material which is wound around the cylindrical member, turning the valve material over, rotating the valve material approximately 90° and repeating the above making a cut.

The present invention still further relates to a method of producing a medical valve, wherein the first and second slits are formed by winding a valve material around a cylindrical member so that one face of the valve material is in tight contact with the outer periphery of the cylindrical member, making a cut substantially perpendicular to the direction of the shaft of the cylindrical member by a cutting means from the other face to the face in tight contact with the cylindrical member of the valve material which is wound around the cylindrical member, rotating the valve material approximately 90° and repeating the above making a cut.

The present invention still further relates to a a catheter with a medical valve, which comprises
a hollow body opened at a distal end thereof; and
a proximal part communicating with a hollow portion of the body and having an introduction passage with the valve therein.

"Cross" or "intersect" as used here includes the crossing of lines or of planes and also partial contact between lines or between planes in a T or X shape.

The present invention has the following advantages ① to ③:

① Since the first slit and the second slit respectively penetrate between the two end faces of the valve, even a tubular member whose inserted distal end portion is thick can easily be inserted into the valve therethrough.

② Each of the first and second slits has openings on the two end faces of the valve and the width of the opening on one end face is shorter than that on the other end face. The opening having the shorter width can assure a high restitutive force of the slit from the open state to the closed state. As a result, the adhesive force of each slit to the periphery of the tubular member when the tubular member is indwelling is increased and fluid leakage can be prevented. Furthermore, the restitutive force of each slit to the closed state when the tubular member is withdrawn is increased, each slit is closed immediately after the tubular member is withdrawn, and fluid leakage can be prevented.

③ The above ① and ② make it possible to provide a medical valve into which a tubular member whose inserted leading portion is thick and whose liquid sealing characteristic is high when the tubular member is indwelling and withdrawn.

The present invention further has the following advantage ④:

④ The first and second slits respectively have an opening portion having the shorter width, which can assure a high restitutive force, mounted on different end faces of the valve. Therefore, the opening portions having the shorter width of the two slits are not concentrated on one end face of the valve, and the inserted area is prevented from being reduced by the concentration. Furthermore, while the liquid sealing characteristic against the tubular member is assured, even a tubular member whose inserted portion is thick can easily be inserted.

The present invention still further has the following advantage ⑤:

⑤ When a thick tubular member is inserted from the side of the end face which has the shorter opening width, it is easy to open the longer opening width, and the thick tubular member can be easily inserted into the valve therethrough even if the slit has a short opening.

The present invention still further has the following advantage ⑥:

⑥ By winding a material of the valve around a cylindrical member, making a cut perpendicular to the direction of the axis of the cylindrical member from one end face to an end face adhering to the cylindrical member of the valve material wound around the cylindrical member by using a cutting means having a standard shape, such as a straight cutting means, turning the valve material over, rotating the valve material approximately 90°, and repeating the above process, a slit with an opening at the longer width at the free end face and an opening having the shorter width at the end face adhering to the cylindrical member can be formed quite easily. In other words, the medical valve of the present invention can be easily produced without using a cutting means having a special shape or a special operation of a cutting means.

The present invention still further has the following advantage ⑦:

⑦ By winding a material of the valve around a cylindrical member, making a cut perpendicular to the direction of the axis of the cylindrical member from one end face to an end face adhering to the cylindrical member of the valve material wound around the cylindrical member by using a cutting means having a standard shape, such as a straight cutting means, rotating the valve material approximately 90°, and repeating the above process, a slit with an opening at the longer width at the free end face and an opening having the shorter width at the end face adhering to the cylindrical member can be formed quite easily. In other words, the medical valve of the present invention can be easily produced without using a cutting means having a special shape or a special operation of a cutting means.

The present invention claimed still further has the following advantage ⑧:

⑧ By mounting the medical valve of the present invention in an introduction passage disposed in the base of the catheter, the above advantages ① to ③ can be obtained and the liquid leakage from the opening of the base can be reliably prevented when the tubular member, such as a guide wire, an injector or an extractor, is inserted into, is indwelling in or is withdrawn from the valve.

The present invention further relates to a catheter assembly, which comprises
a catheter; and a connecting instrument, the catheter including a hollow body introducible into the blood vessel, and a proximal part communicating with a hollow portion of the body and having an introduction passage with a valve therein, the connecting instrument including a tubular portion capable of being connected to the introduction passage of the base of the catheter and capable of being inserted in a liquid sealing manner through the valve of the introduction passage, wherein the distal end of the tubular portion of the connecting instrument is disposed adjacent to an inner surface of the body of the catheter in the state in which the connecting instrument is connected to the introduction passage of the catheter.

The present invention still further relates to a catheter assembly, wherein the inner surface of the tubular portion of the connecting instrument is tapered so that the diameter thereof is decreased toward the distal end thereof.

The present invention still further relates to a catheter assembly, wherein the tapering angle at which the inner surface of the tubular portion of the connecting instrument is tapered is 5 to 15 degrees.

A catheter assembly according to the present invention is used with its body of the catheter being percutaneously inserted into the blood vessel.

When an cardiopulmonory bypass operation is to be performed during PTCA or IABP heart treatment or during the treatment of acute heart failture, e.g. myocardial infarction, a connecting instrument is inserted into the introduction passage of the catheter. The hemostatic valve in the passage allows the connecting instrument to be inserted in a liquid tight manner and without involving any blood leakage.

When the catheter assembly is on the blood-drawing side, the associated connecting instrument is connected with a blood-drawing line of the extracorporeal circulation circuit so that blood in the patient's body is drawn out to the circuit through the catheter body and the tubular portion of the connecting instrument.

When the catheter assembly is on the blood pumping-in side, the associated connecting instrument is connected with a blood pumping-in line of the circuit so that the extracorporeally circulated blood is pumped into the blood vessel through the tubular portion of the connecting instrument and the catheter body.

According to the present invention a tubular distal end portion of a connecting instrument penetrating the valve of the catheter is disposed adjacent to the inner surface of the body of the catheter. Therefore, the tubular distal end portion of the connecting instrument and the body of the catheter form a blood passage which extends almost smoothly, so that it is unlikely that the flow of the blood will be disturbed and it is possible to reduce the resistance of the flow of the blood, thereby reducing the pressure loss. As a result, a catheter assembly of the present invention which has a diameter small enough to facilitate the percutaneous insertion of the catheter assembly is capable of reducing the pressure loss, thereby assuring sufficient amounts of drawn-out or pumped-in blood.

Furthermore, according to the present invention, when the catheter assembly is used on the side of the blood-drawing line, since the area of the blood passage formed by the tubular portion of the connecting instrument is gradually widened in the direction of the flow of the blood, it is possible to reduce the pressure loss, thereby assuring sufficient amounts of drawn-out blood.

BEST MODE FOR CARRYING OUT THE INVENTION

Figure 1A:
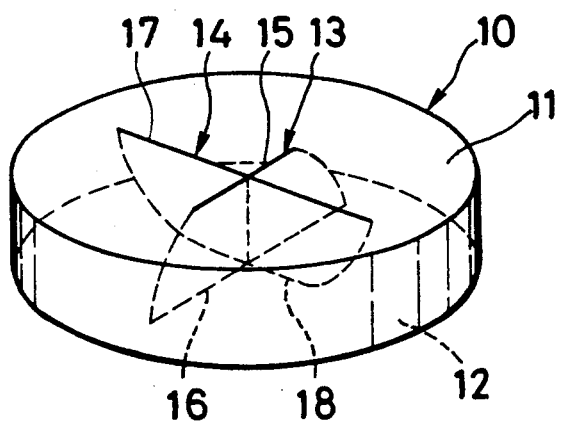
FIGS. 1 (A), (B), (C) is a schematic view of a medical valve according to a first embodiment of the present invention.
Figure 1B:
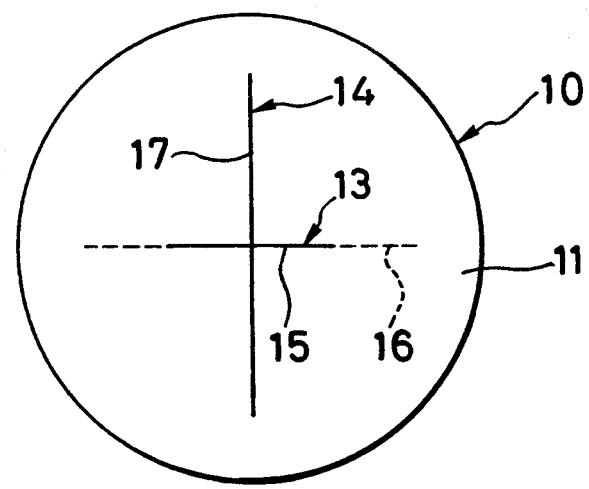
Figure 1C:
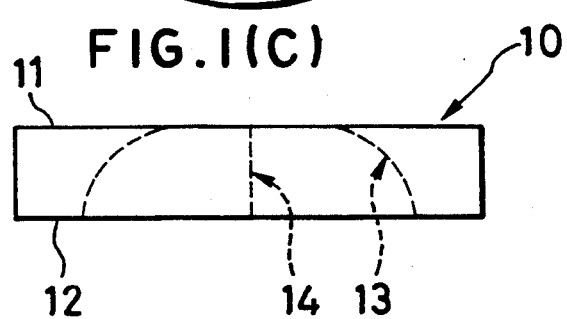

First Embodiment of Valve (See FIG. 1)

A valve 10 is made of a flexible elastic material and crosses a first slit 13 disposed from one end face 11 to the other end face 12 and a second slit 14 disposed from the one end face 11 to the other end face 12 so as to make a cross. In the valve 10, a first opening width 15 which the first slit 13 has on the end face 13 is shorter than a second opening width 16 which the first slit 13 has on the end face 12, and a first opening width 17 which the second slit 14 has on the end face 11 is longer than a second opening width 18 which the second slit 14 is has on the end face 12. In other words, in the valve 10, the end face (11) which has the shorter opening width 15 of the two opening widths 15 and 16 of the first slit 13 and the end face (12) which has the shorter opening width 18 of the two opening widths 17 and 18 of the second slit 14 are different from each other.

For the flexible elastic material of the valve 10, synthetic rubber, such as silicone rubber, urethane rubber and fluoro rubber, natural rubber and the like are suitable.

The above valve 10 has the following advantages ① to ④:

① Since both first slit 13 and the second slit 14 penetrate the two end faces 11 and 12 of the valve 10, even a tubular member whose inserted distal end portion is thick can be easily inserted into the valve 10 therethrough.

② The one opening widths (15 and 18) of the first and second slits 13 and 14 on the two end faces 11 and 12 are shorter than the other opening widths (16 and 17), and the shorter opening widths can assure a high restitutive force of the slits 13 and 14 from the open state to the closed state. As a result, the slits 13 and 14 adhere strongly to the periphery of the tubular member when the tubular member is indwelling therein, thereby preventing fluid leakage. Furthermore, the restitutive force of the slits 13 and 14 to the closed state when the tubular member is withdrawn is increased and the slits 13 and 14 are closed immediately after the tubular member is withdrawn, thereby preventing fluid leakage.

③ The above ① and ② allow the intersection of a tubular member whose inserted distal end portion is thick, and a valve 10 having a high liquid sealing characteristic can be provided.

④ The shorter opening widths (15 and 18) of the first and second slits 13 and 14 which can assure a high restitutive force are disposed on different end faces 11 and 12 of the valve 10, and are not, therefore, concentrated on one end face of the valve. Thereby it is possible to prevent the insertion area from being reduced by the concentration, assure a sufficient liquid sealing characteristic for the tubular member, and furthermore, easily insert even a tubular member whose inserted distal end portion is thick into the valve 10.

Figure 2:
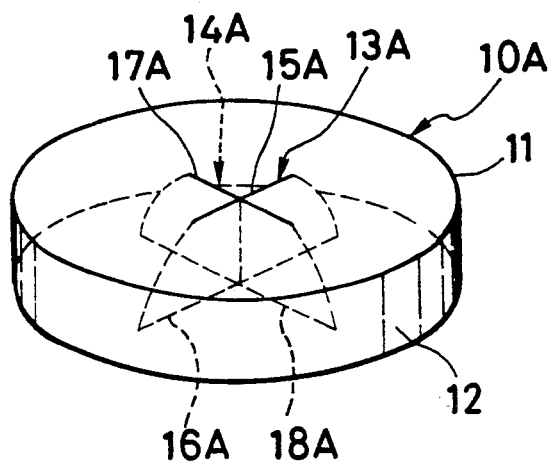
FIG. 2 is a schematic view of a medical valve according to a second embodiment of the present invention.

Second Embodiment of Valve (See FIG. 2)

A valve 10A crosses, in the same manner as the above valve 10, a first slit 13A disposed from one end face 11 to the other end face 12 and a second slit 14A disposed from the one end face 11 to the other end face 12 so as to make a cross. In the valve 10A, a first opening width 15A which the first slit 13A has on the end face 11 is shorter than a second opening width 16A which the first slit 13A has on the end face 12, and a first opening width 17A which the second slit 14A has on the end face 11 is shorter than a second opening width 18A which the second slit 14A has on the end face 12.

Therefore, the valve 10A has the above-mentioned advantages ① and ③ which the valve 10 has.

However, the valve 10A does not have the above advantage ④ which the valve 10 has since the shorter opening width 15A of the two opening widths 15A and 16A of the first slit 13A and the shorter opening width 17A of the two opening widths 17A and 18A of the second slit 14A are disposed on the same end face (11).

On the occation of the thick tubular member is inserted from the side of the end face 11 which has the shorter opening width 15A, 17A, it is easy to open the longer opening width 16A, 18A, and the thick tubular member can be easily inserted into the valve therethrough even if the slit has a short opening.

Figure 3:
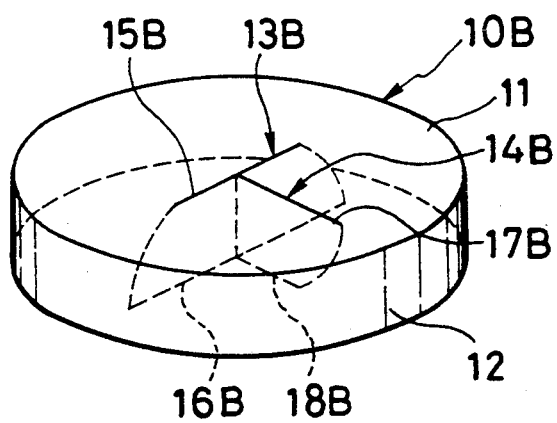
FIG. 3 is a schematic view of a medical valve according to a third embodiment of the present invention.

Third Embodiment of Valve (See FIG. 3)

A valve 10B crosses a first slit 13B disposed between the one end face 11 and the other end face 12 and a second slit 14B disposed between the one end face 11 and the other end face 12 so as to form a T shape. Furthermore, in the valve 10B, a first opening width 15B. which the first slit 13B has on the end face 11 is shorter than a second opening width 16B which the first slit 13B has on the end face 12, and a first opening width 17B which the second slit 14B has on the end face 11 is longer than a second opening width 18B which the second slit 14B has on the end face 12. In other words, in the same manner as the valve 10, the end face (11) which has the shorter opening width 15B of the two opening widths 15B and 16B of the first slit 13B and the end face (12) which has the shorter opening width 18B of the two opening widths 17B and 18B of the second slit 14B are different from each other in the valve 10B.

Figure 4A:
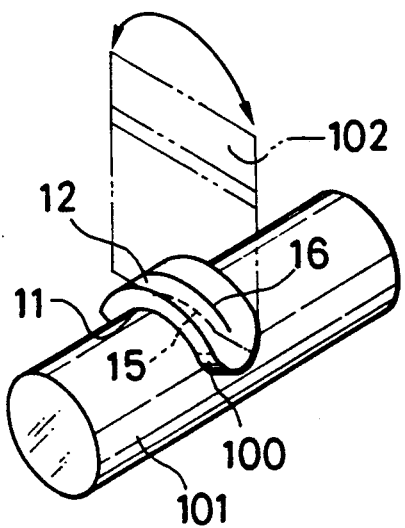
FIGS. 4 (a), (b), (c) is a schematic view showing an example of a method of producing the valve of the present invention.
Figure 4B:
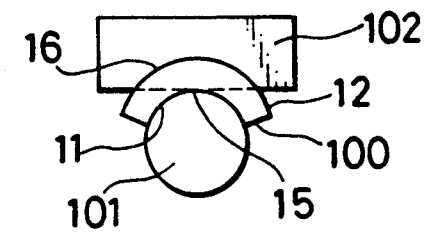
Figure 4C:
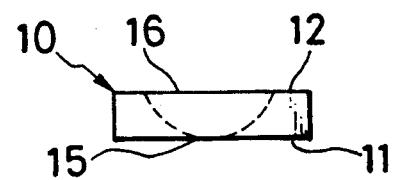

Therefore, the valve 10B has the above-mentioned advantages ① and ④ which the valve 10 has. (Embodiment of Method of Producing Valve) (See FIG. 4)

The valve 10 (10A, 10B) are produced by, for example, the following method:

(1) A valve material 100 is wound around a cylindrical member 101 so that one end face 11 of the valve material 100 is in tight contact with the peripheral surface of the cylindrical member 101.

(2) A cut perpendicular to the direction of the shaft of the cylindrical member 101 is made by a cutter 102 from a free end face 12 to the end face in tight contact with the cylindrical member 101 of the valve material 100 which is wound around the cylindrical member 101. Then, the valve material 100 is turned over and rotated approximately 90 and the above process is performed.

At that time, an opening width is also formed on the end face in contact with the cylindrical member 101 by inserting the cutting blade of the cutter 102 more deep inside the cylindrical member 101 or swinging the cutting blade of the cutter 102 in contact with the surface of the cylindrical member 101.

The above method has the following advantage ⑤:

⑤ By winding the valve material 100 around the cylindrical member 101 and making a cut from the free end face 11 to the end face 12 of the valve material 100 in tight contact with the cylindrical member 101 by the cutter 102 which has a normal shape, such as a straight cutting blade, it is possible to quite easily form a slit which has the longer opening width on the free end face 11 and the shorter opening width on the end face 12. In other words, the above first and second slits 13 and 14 can be formed and the valve 10 can be produced without using a cutter having a special shape or a special operation of a cutter.

First Embodiment of Catheter Assembly Using Catheter with Valve (See FIGS. 5 to 8)

A catheter 20 is comprises a medical valve 10 and constitutes a catheter assembly 1 in combination with a connecting instrument 30. The catheter assembly 1 additionally comprises a dilator 40.

Figure 5:
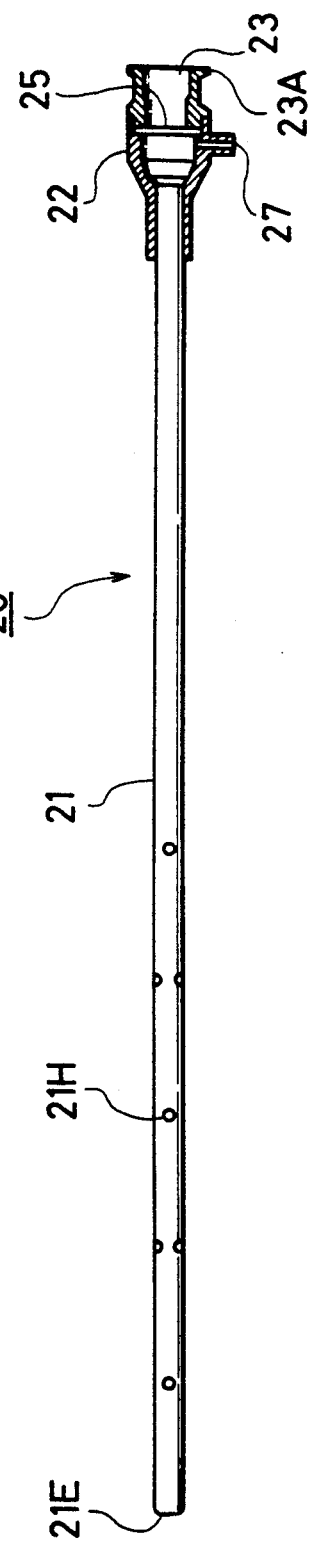
FIG. 5 is a schematic view of a catheter with a valve of the present invention.

The catheter 20 comprises, as shown in FIG. 5, a body 21 and a proximal end 22.

The body 21 of the catheter 20 is used in the state of being percutaneously inserted into the blood vessel. The catheter body 21 has an opening 21E at the distal end (hereinafter referred to as "the distal-end hole"), and a plurality of side holes 21H.

The proximal end 22 of the catheter 20 is joined to one end portion of the catheter body 21 to communicate therewith, and has an introduction passage 23. The introduction passage 23 has a above-mentioned valve 10 (10A, 10B) which is disposed in an opening portion of the passage 23 and provided to prevent leakage of blood from the catheter body 21 to the outside.

The proximal end 22 also has a sub-passage 27 capable of communicating with a tube having a cock at one end thereof, so as to function as a port which may be used to inject a medicine liquid or collect blood.

The catheter 20 should preferably have an inner diameter of the body 21 which is within the range from 2 to 10 mm in order to facilitate the percutaneous insertion of the catheter body 21. If this inner diameter is less than 2 mm, there is a risk that, during emergency auxiliary circulation, the amount of drawn-out or sent-in blood may fall short of the necessary amount. If the inner diameter exceeds 10 mm, the percutaneous insertion of the catheter 20 will be difficult.

The catheter 20 has the following arrangement. When the opening area of the distal-end hole 21E of the catheter body 21 is expresed as S1, and the total opening area of the side holes 21H is expressed as S2 (S2=N×Sh if there are N side holes 21E which each have an area of Sh), the relation of $2 \times S1 \geq S2 \geq 0.5 \times S1$ is satisfied. In other words, the total opening area S2 of the side holes 21H ranges from $\frac{1}{2}$ to 2 times of the opening area S1 of the distal-end hole 21E. If S2 is smaller than $\frac{1}{2} \times S1$, when the catheter is on the blood-drawing side, the amount of blood drawn from the region where the side holes open, i.e., from the vena cava, will be insufficient. If S2 is greater than $2 \times S1$, the amount of the blood drawn from the superior vena cava will be insufficient.

Figure 9:
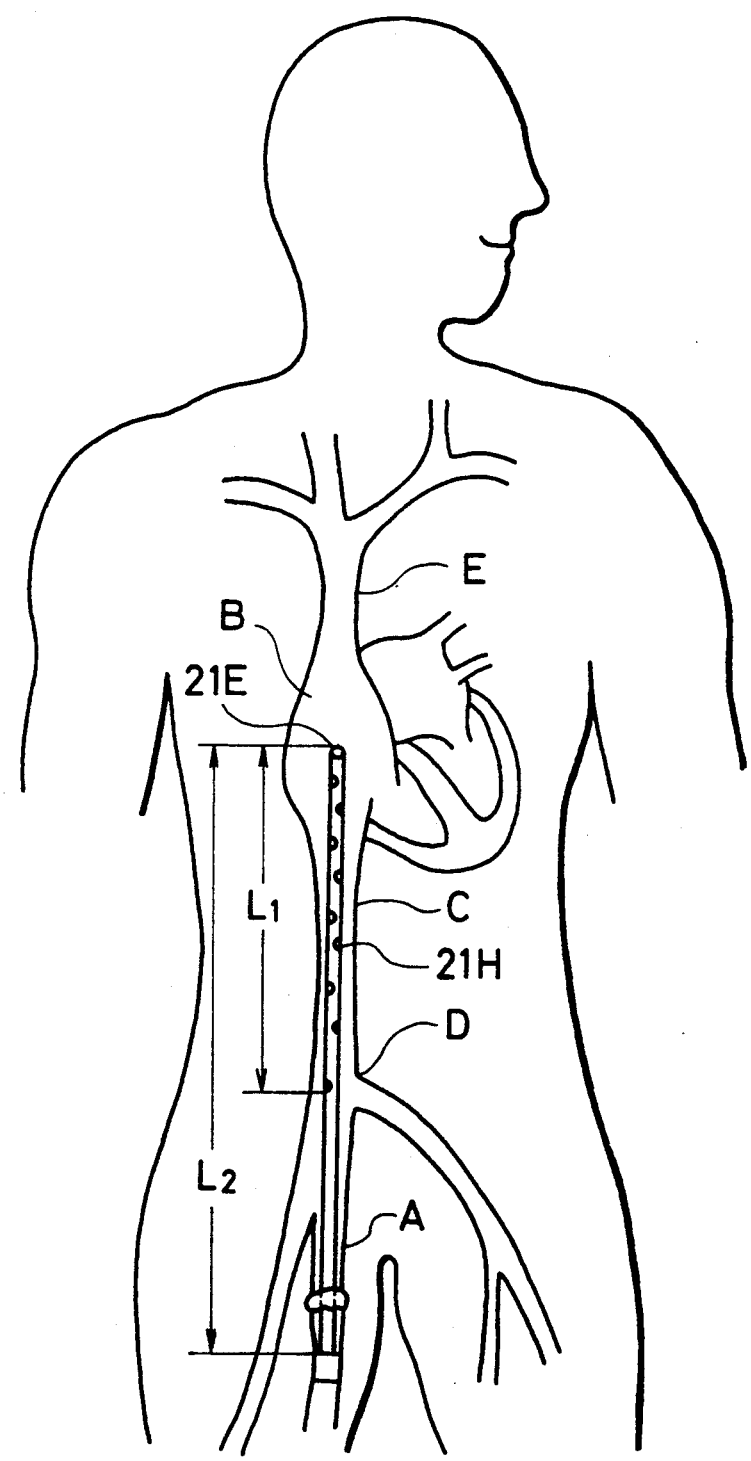
FIG. 9 is a schematic view showing an indwelling state of the catheter with the valve.

The position at which the side holes 21H are indwelt should preferably be as follows. If the catheter 20 is inserted into the femoral vein A, as shown in FIG. 9, the side holes 21H should be positional within the inferior vena cava C and in the region from the entrance of the right atrium B to the bifurcation D of the inferior vena cava C (the symbol E designating the superior vena cava). This is because, in this region, blood flows in such a sufficient amount as to assure the drawing of the necessary amount of blood. Therefore, if this position of the side holes 21H relative to the patient's body is translated into their position relative to the catheter body 21 itself, the following can be said. The whole length L2 of the catheter body 21 must correspond to the sum of the first distance from the right atrium to the bifurcation of the inferior vena cava, the second distance from the bifurcation to the position where the catheter is percutaneously inserted into the femoral vein, and an additional length α of the catheter 20 outside the patient's body. In the case where the patient's body has a first distance of 30 to 40 cm and a second distance of 15 to 20 cm, the required whole length L2 of the catheter body 21 is 60 cm. In this case, in order to assure the necessary amount of drawn-out blood, the side holes 21H should preferably be positioned occupying a length from the distal end of the catheter body 21 which is 40 cm at most. Therefore, the whole length L2 of the catheter body 21 should satisfy the following relation with the distance L1 from the distal end of the catheter body 21 to the side hole closest to the proximal end 22: $\frac{2}{3} \times L2 \geq L1$. In the case where the patient's body is relatively small the patient requiring extacorporeal circulation by the use of the catheter according to the present invention often has a relatively small body), and where the first distance is about $\frac{2}{3}$ of the corresponding hemostatic value in above-described case, i.e., about 20 cm, the whole length L2 and the distance L1 should satisfy the relation of $L1 \geq \frac{1}{3} \times L2$. Thus, it is preferable that the whole length L2 and the distance L1 should satisfy the relation expressed as follows:

$$\tfrac{2}{3} \times L2 \geq L1 \geq \tfrac{1}{3} \times L2$$

If the catheter 20 satisfies this relationship it is possible to attain the necessary amount of blood drawn whether the patient's body is large or small.

The catheter body 21 is made of a material such as a fluoroplastic, polyethylene, polypropylene, or a polyester-based elastomer. The proximal end 22 is made of a material such as polyethylene, polypropylene, polyamide, polycarbonate, or polystyrene.

Figure 6:
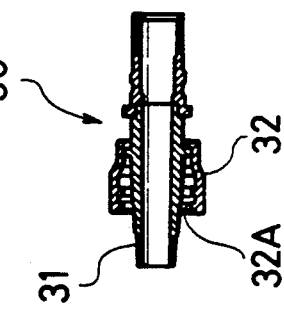
FIG. 6 is a sectional view of the essential parts of an example of a connecting instrument used in combination with the catheter with the valve of the present invention.

As shown in FIG. 6, the connecting instrument 30 has a tubular portion 31 which can be connected with the introduction passage 23 in the proximal end 22 of the catheter 20, and be inserted in a liquid tight manner through the valve 10 in the introduction passage 23. The other end of the tubular portion 31 is connected with the blood drawing-out or pumping-in line of the extracorporeal circulation circuit. The connecting instrument 30 also has a threaded connecting cap 32 on the outer periphery of the tubular portion 31. When a female screw 32A of the connecting cap 32 is threaded onto a male screw 23A provided around the introduction passage 23 of the proximal end 22, the connecting instrument 30 is fixed to the catheter 20.

Figure 8:
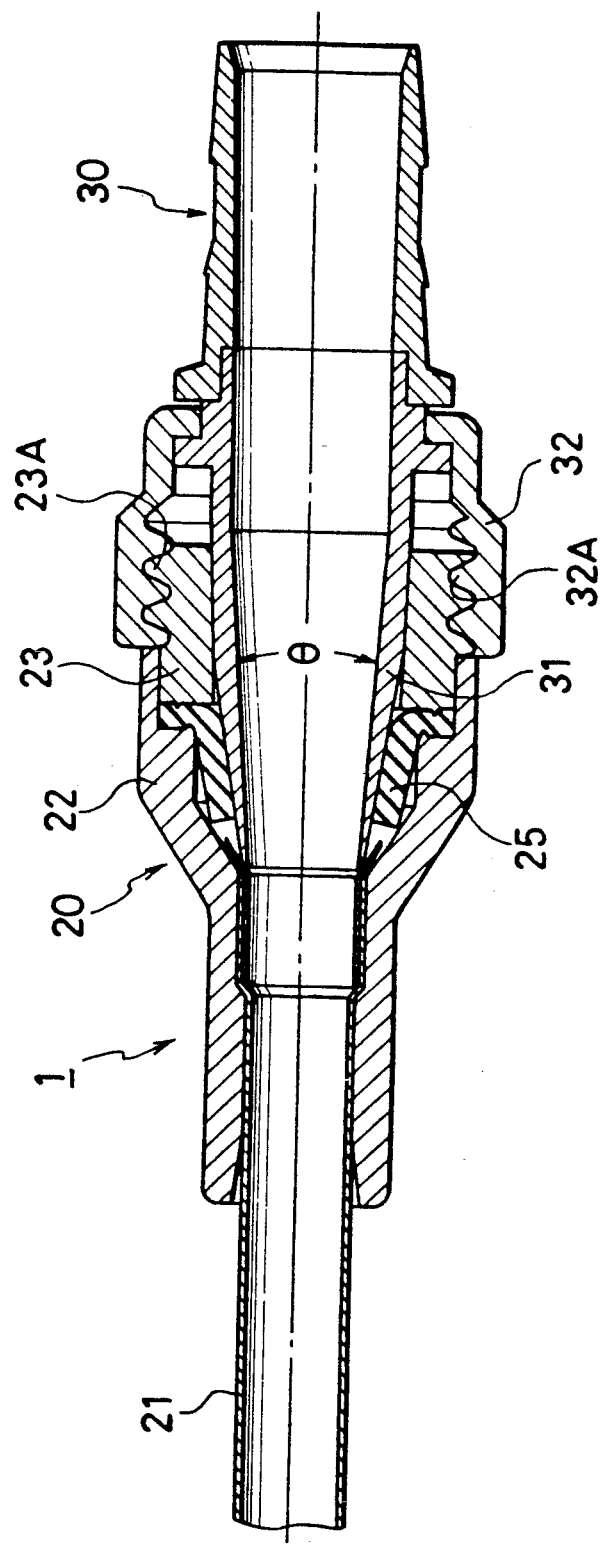
FIG. 8 is a sectional view showing a state of use of a catheter assembly.

The catheter assembly 1 is such that, when the connecting instrument 30 is connected with the introduction passage 23 of the catheter proximal end 22, as shown in FIG. 8, the distal end of the tubular portion 31 of the connecting instrument 30 is disposed adjacent to the inner surface of the catheter body 21. In this embodiment, that distal end abuts on the inner surface of the catheter body 21.

The inner surface of the tubular portion 31 of the connecting instrument 30 is tapered, more specifically, converged with its diameter decreasing toward the distal end of the portion 31.

The tapering angle θ (in FIG. 8) at which the inner surface of the tubular portion 31 is tapered should preferably be 5 to 15 degrees.

If the tapering angle q is less than 5 degrees, since the section of the passage is widened in the direction of the flow of the blood, it is difficult to reduce the pressure loss. If the tapering angle q exceeds 15 degrees, the inner diameter of the tubular portion 31 connected to the connecting instrument 31 is increased and the priming volume is increased.

The tubular portion 31 of the connecting instrument 30 is made of a material such as polycarbonate, a vinyl chloride resin, or polypropylene, while the cap 32 is made of a material such as polyamide, polycarbonate, or a vinyl chloride resin.

Figure 7:
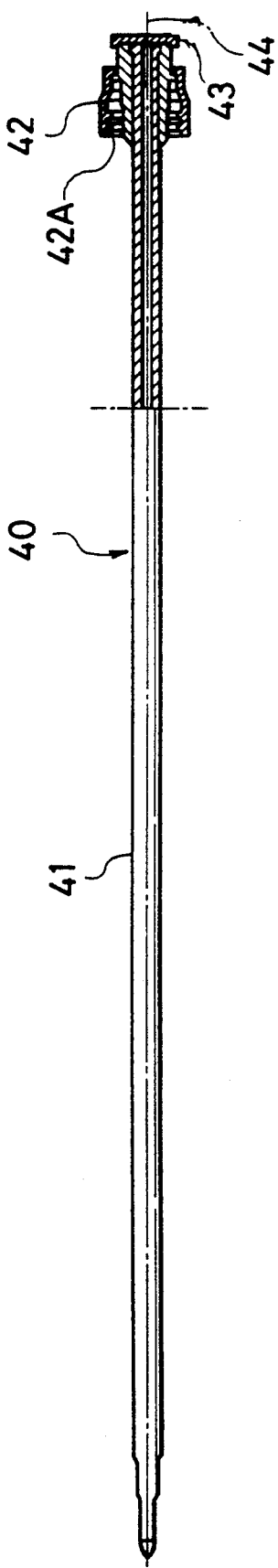
FIG. 7 is a sectional view of an example of a dilator used in combination with the catheter with the valve of the present invention.

The dilator 40 is capable of being inserted into and through the valve 10 of the introduction passage 23 of the proximal end 22 of the catheter 20 as well as the body 21 of the catheter 20 so as to lead the catheter body 21 into the blood vessel. As shown in FIG. 7, the dilator 40 comprises a body 41 and a proximal end with a threaded connecting cap 42 provided around the proximal end. When a female screw 42A of the connecting cap 42 is threaded onto the male screw 23A provided around the introduction passage 23 in the catheter base, 22 the dilator 40 is integrated with the catheter 20. The body 41 of the dilator 40 is capable of being inserted in a liquid tight manner through the valve 10 in the introduction passage 23 of the catheter 20. The dilator 40 also has a hemostatic valve 43 provided at the outer end of the cap 42. The dilator 40 allows the insertion therethrough of a mini guide wire 44 when the wire 44 is passed through the hemostatic valve 43 in a liquid tight manner.

The dilator body 41 is made of a material such as polyethylene, polypropylene, or a polyester-based elastomer, while the connecting cap 42 is made of a material such as polyamide, polycarbonate, or a vinyl chloride resin.

The catheter 20 of the above-described catheter assembly 10 is inserted into and indwelt in the blood vessel in the following manner:

(1) An indwelling needle having an outer needle member and an inner needle member fit therein is percutaneously inserted into the blood vessel.

(2) The inner needle member is removed. The mini guide wire 44 is passed through the outer needle member to be indwelt in the blood vessel. After the indwelling, the outer needle member is removed.

(3) The catheter 20 and the dilator 40 integrated therewith are inserted into the blood vessel while they are guided by the mini guide wire 44. After the insertion, the mini guide wire 44 and the dilator 40 are removed, thereby indwelling the catheter 20 in the blood vessel.

At this time, the body 41 of the dilator 40 is capable of being inserted in a liquid sealing manner through the valve 10 in the introduction passage 23 of the catheter 20. When the dilator 40 is indwelling, the two slits 13 and 14 are in tight contact with the outer periphery of the body 41 as described above and prevent the blood from leaking. When the dilator 40 is withdrawn, the two slits 13 and 14 are closed by their strong restitutive force to the closed state immediately after the dilator 40 is withdrawn, thereby preventing the blood from leaking.

The catheter 20 indwelt in the blood vessel is used in the following manner:

(1) When auxiliary blood circulation is to be performed during PTCA or IABP heart treatment or during the treatment of acute myocardial infarction or heart failure, the connecting instrument 30 is inserted into the introduction passage 23 of the catheter 20. At this time, the connecting instrument 30 is capable of being inserted in a liquid sealing manner through the valve 10 in the introduction passage 23 of the catheter 20, and the two slits 13 and 14 are in tight contact with the periphery of the connecting instrument 30 as described above so as to prevent the blood from leaking.

(2) The connecting instrument 30 of the catheter assembly 1 on the blood-drawing side is connected with the blood-drawing line of the extracorporeal circulation circuit so that blood is drawn from the patient's body through the catheter body 21 and the tubular portion 31 of the connecting instrument 30.

(3) The connecting instrument 30 of the catheter assembly 10 on the blood pumping-in side is connected with the blood pumping-in line of the extracorporeal circulation circuit so that the extracorporeally circulated blood is pumped into the blood vessel through the tubular portion 31 of the connecting instrument 30 and the catheter body 21.

The catheter 20 according to the present invention can be percutaneously inserted into the femoral vein in such a manner that the distal-end hole 21E of the catheter body 21 is positioned in the vicinity of the right atrium, and can be connected with the blood-drawing line of the extracorporeal circulation circuit so as to draw blood from the right atrium and the venae cavae. At this time, the position of the side holes 21H of the catheter body 21 is such that the holes 21H are distributed from the vicinity of the bifurcation of the inferior vena cava to the vicinity of the right atrium.

(4) When the above auxiliary blood circulation is completed, the connecting instrument 30 is withdrawn from the introduction passage 23 of the catheter 20.

Then, the valve 10 in the introduction passage 23 through which the connecting instrument 30 is withdrawn is closed by a strong restitutive force of the slits 13 and 14 to the closed state immediately after the connecting instrument 30 is withdrawn, so that blood leakage can be prevented.

Therefore, the above catheter 20 with the valve has the following advantage ⑥:

⑥ Since the medical valve 10 of the present invention is mounted in the introduction passage 23 disposed in the base of the catheter 20 and the body 41 of the dilator 40 or the connecting instrument 30 is inserted into the valve 10, the above advantages ① to ④ which the valve 10 has can be obtained and the blood is reliably prevented from leaking from the opening of the base of the catheter 20 when the body 41 or the connecting instrument 30 is indwelling in or withdrawn from the catheter 20.

In carrying out the present invention, the valve in the introduction passage of the base of the catheter with the valve may allow the insertion of insertion bodies other than the connecting instrument connected to the blood-drawing and blood-transfusion lines of the extracorporeal blood circulation circuit. For example, a catheter for heart treatment (a guide catheter, a balloon catheter guided by the guide catheter, and so on), or a connecting instrument connected to a medicine liquid supply line may be inserted into the valve.

Furthermore, in carrying out the present invention, the slits of the valve may form a twisted plane between the two end faces.

The catheter assembly 1 has the following advantages ⑦ and ⑧:

⑦ The distal end of the tubular portion 31 of the connecting instrument 30, which is penetrating the hemostatic valve 25 of the catheter 20, is disposed adjacent to the inner surface of the body 21 of the catheter 20. Therefore, the tubular portion 31 of the connecting instrument 30 and the body 20 of the catheter 20 form a smoothly elongated blood passage, so that it is unlikely that the flow of the blood is disturbed and it is possible to reduce the resistance of the flow of the blood, thereby reducing the pressure loss. Therefore, the catheter assembly 1, whose diameter is small enough to facilitate the percutaneous insertion of the catheter assembly 1, is capable of reducing the pressure loss, hence, of assuring sufficient amount of drawn-out or pumped-in blood.

⑧ When the catheter assembly 1 is used on the side of the blood-drawing line, since the area of the blood passage, which is formed by the tubular portion 31 of the connecting instrument 30, is gradually widened in the direction of the flow of the blood, it is also possible to reduce the pressure loss, thereby assuring sufficient amount of drawn-out blood.

According to the above-described embodiment, since the catheter 20 has the sub-passage 27 at the base 22, it is possible to use the passage 27 to perform the injection of a medicine liquid or the collection of blood simultaneously with heart treatment or the like.

In carring out the present invention, the introduction passage of the base of the catheter may allow the insertion of an insertion body other than the connecting instrument connected with the blood-drawing line or the blood pumping-in line of the extracorporeal circulation circuit. For instance, a catheter for heart treatment (e.g., a unit having a guide catheter and a balloon catheter guided theterby), or a connecting instrument connected with a medicine liquid supply line may be inserted into the introduction passage.

Figure 10:
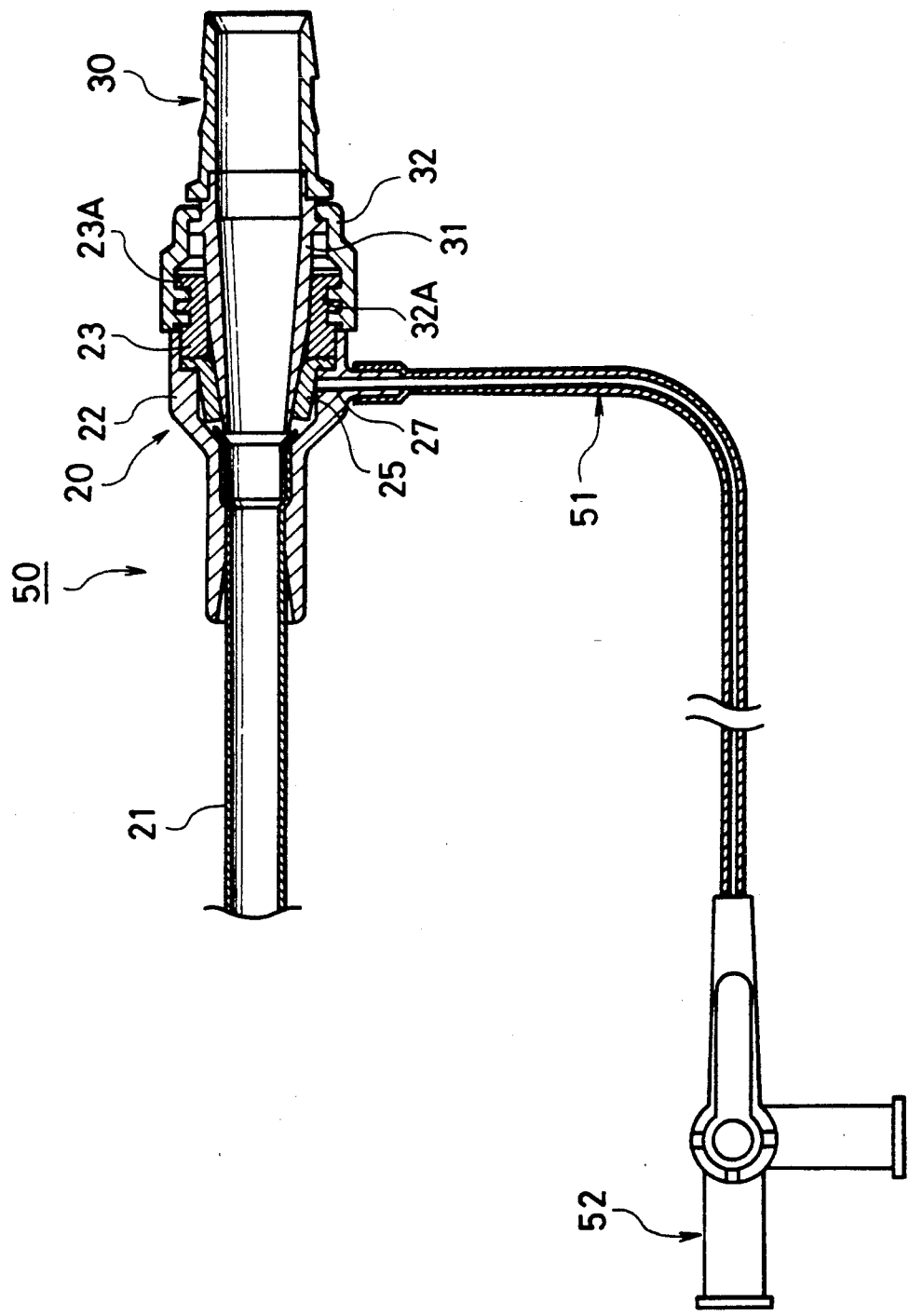
FIG. 10 is a sectional view showing another state of use of the catheter assembly.

Second Embodiment of Catheter Assembly (See FIG. 10)

A catheter assembly 50, shown in FIG. 6, is a modification of the above-described catheter assembly 10. Similarly to the catheter assembly 10, the catheter assembly 10 basically comprises a catheter 20 and a connecting instrument 30, and additionally comprises a dilator 40.

The substantial difference of the catheter assembly 50 from the catheter assembly 10 is that when the connecting instrument 30 is connected to the introduction passage 23 of the catheter 20, the distal-end of the tubular portion 31 of the connecting instrument 30 does not abut on the inner surface of the body 21 of the catheter 20, but is disposed close to the inner surface with a certain gap.

Therefore, with the catheter assembly 50, when the sub-passage 27 in the proximal end 22 of the catheter 20 is connected through a side tube 51 and a three-way cock 52 to a pressure transducer (not shown) so as to measure the blood pressure, the blood pressure introduced by the catheter body 21 can be applied to the sub-passage 27 through the gap between the inner surface of the body 21 and the distal-end of the tubular portion 31, thus without any substantial resistance. This enables highly precise pressure measurement.

In the catheter assembly of the present invention, not only the above valve 10 but also valves having other shapes may be widely applied.

Effect of the Invention

As has been above, according to the present invention, there is provided a medical valve into which even a tubular member whose inserted distal end portion is thick can be inserted and whose liquid sealing characteristic is high both when the tubular member is indwelling and when the tubular member is withdrawn.

According to the present invention, there is provided a method which can easily produce the above valve.

According to the present invention, there is further provided a catheter which has the above valve and which can with certainty prevent fluid from leaking from an opening at its proximal part.

According to the present invention, there is still further provided a catheter assembly that has a diameter small enough to facilitate percutaneous insertion at the time of circulatory support but that is capable of assuring sufficient amounts of drawn-out and pumped-in blood.

What is claimed is:

1. A medical valve comprising:
   a valve member made of a flexible elastic material and having at least two faces;
   a first slit disposed between a first face of said at least two faces and a second face of said at least two faces; and
   a second slit disposed between said first face and said second face;
   wherein said first slit and said second slit intersect each other;
   wherein a first opening width of said first slit on said first face is different from a second opening width of said first slit on said second face; and
   wherein a first opening width of said second slit on said first face is different from a second opening width of said second slit on said second face.

2. A medical valve according to claim 1, wherein:
   the first opening width of said first slit on said first face is longer than the second opening width of said first slit on said second face; and
   the second opening width of said second slit on said second face is longer than the first opening width of said second slit on said first face.

3. A medical valve according to claim 2, wherein said first and second slits cross each other.

4. A medical valve according to claim 2, wherein one of said first and second slits terminates at the other of said first and second slits.

5. A medical valve according to claim 1, wherein:
   the first opening width of said first slit on said first face is longer than the second opening width of said first slit on said second face; and
   the first opening width of said second slit on said first face is longer than the second opening width of said second slit on said second face.

6. A medical valve according to claim 5, wherein said first and second slits cross each other.

7. A medical valve according to claim 5, wherein one of said first and second slits terminates at the other of said first and second slits.

8. A medical valve according to claim 1, wherein said first and second slits cross each other.

9. A medical valve according to claim 1, wherein one of said first and second slits terminates at the other of said first and second slits.

10. A catheter with a medical valve, comprising:
    an elongated hollow body having an opening at a distal end thereof;
    a proximal member coupled to a proximal end of said hollow body, said proximal member having an introduction passage and communicating with the interior of said hollow body; and
    a medical valve disposed in said introduction passage of said proximal member, said medical valve comprising:
      a valve member made of a flexible elastic material and having at least two faces;
      a first slit disposed between a first face of said at least two faces and a second face of said at least two faces; and
      a second slit disposed between said first face and said second face;
      wherein said first slit and said second slit intersect each other;
      wherein a first opening width of said first slit on said first face is different from a second opening width of said first slit on said second face; and
      wherein a first opening width of said second slit on said first face is different from a second opening width of said second slit on said second face.

11. A catheter assembly with a medical valve, comprising:
    a catheter including a hollow body introducible into a blood vessel, and a proximal member having an introduction passage and communicating with the interior of said hollow body;
    a medical valve disposed in said introduction passage, said medical valve comprising:
      a valve member made of a flexible elastic material and having at least two faces;

a first slit disposed between a first face of said at least two faces and a second face of said at least two faces; and a second slit disposed between said first face and said second face;

wherein said first slit and said second slit intersect each other;

wherein a first opening width of said first slit on said first face is different from a second opening width of said first slit on said second face; and wherein a first opening width of said second slit on said first face is different from a second opening width of said second slit on said second face; and a connecting instrument including a tubular portion connectable to said introduction passage and insertable in a liquid sealing manner through said medical valve disposed in said introduction passage, wherein a distal end of said tubular portion of said connecting instrument is disposed adjacent to an inner surface of the interior of said hollow body of said catheter when said tubular portion is inserted through said medical valve to be connected to said introduction passage of said proximal member of said catheter.

12. A catheter assembly with a medical valve according to claim 11, wherein:

the first opening width of said first slit on said first face is longer than the second opening width of said first slit on said second face; and the second opening width of said second slit on said second face is longer than the first opening width of said second slit on said first face.

13. A catheter assembly with a medical valve according to claim 11, wherein:

the first opening width of said first slit on said first face is longer than the second opening width of said first slit on said second face; and the first opening width of said second slit on said first face is longer than the second opening width of said second slit on said second face.

14. A catheter assembly according to claim 11, wherein said tubular portion of said connecting instrument is tapered so that the diameter thereof is decreased toward the distal end thereof.

15. A catheter assembly according to claim 14, wherein said tubular portion of said connecting instrument tapers at a tapering angle from 5 to 15 degrees.

16. A catheter assembly according to claim 14, wherein said tapered tubular portion of said connecting instrument contacts said valve disposed in said introduction passage of said proximal member of said catheter.

* * * * *